United States Patent [19]
Graser et al.

[11] Patent Number: 5,880,353
[45] Date of Patent: Mar. 9, 1999

[54] GAS SENSOR

[75] Inventors: Theodor Graser; Gerhard Hoetzel; Johann Wehrmann; Heinz Eisenschmid, all of Stuttgart, Germany

[73] Assignee: Robert Bosch GmbH, Stuttgart, Germany

[21] Appl. No.: 945,297

[22] PCT Filed: Nov. 20, 1996

[86] PCT No.: PCT/DE96/02210

§ 371 Date: Oct. 14, 1997

§ 102(e) Date: Oct. 14, 1997

[87] PCT Pub. No.: WO97/33165

PCT Pub. Date: Sep. 12, 1997

[30] Foreign Application Priority Data

Mar. 6, 1996 [DE] Germany .................. 196 08 544.6

[51] Int. Cl.⁶ .................. G01N 27/58; H01L 7/00; B60H 1/32
[52] U.S. Cl. .................. 73/23.2; 73/23.31; 73/31.05; 422/94
[58] Field of Search .................. 73/23.2, 23.31, 73/31.05; 422/94; 338/34

[56] References Cited

U.S. PATENT DOCUMENTS

| | | | |
|---|---|---|---|
| 4,199,424 | 4/1980 | Teitelbaum | 204/195 S |
| 4,223,293 | 9/1980 | Springer et al. | 338/34 |
| 4,225,842 | 9/1980 | Schlesselman et al. | 338/34 |
| 4,322,968 | 4/1982 | Takami et al. | 73/27 R |
| 4,606,219 | 8/1986 | Bout et al. | 73/23 |
| 4,736,618 | 4/1988 | Usami et al. | 73/23 |
| 4,883,643 | 11/1989 | Nishio et al. | 422/94 |
| 4,995,256 | 2/1991 | Norlien et al. | 73/31.04 |
| 5,117,216 | 5/1992 | McQueen | 338/24 |
| 5,377,528 | 1/1995 | Dauvergne et al. | 73/31.01 |
| 5,585,547 | 12/1996 | Kim et al. | 73/31.05 |
| 5,616,825 | 4/1997 | Achey et al. | 73/23.31 |
| 5,663,488 | 9/1997 | Wang et al. | 73/23.25 |

*Primary Examiner*—Hezron Williams
*Assistant Examiner*—J. David Wiggins
*Attorney, Agent, or Firm*—Kenyon & Kenyon

[57] ABSTRACT

A gas sensor having a sensor element which is immobilized in gas-tight fashion in a metal housing. The gas sensor has a double-walled protective tube with an outer protective sleeve and an inner protective sleeve, each of which possesses openings for the entry and/or exit of gas. The inner protective sleeve forms a gas space into which the sensor element projects with a section at the measurement-gas end. The outer protective sleeve is a sleeve having a closed enveloping surface, the openings for the entry and/or exit of gas being arranged in the cavity at the end face of the sleeve. The gas space formed by the inner protective sleeve has, perpendicular to the extension direction of the sensor element, a rectangular cross section.

14 Claims, 3 Drawing Sheets

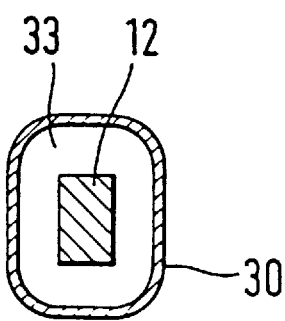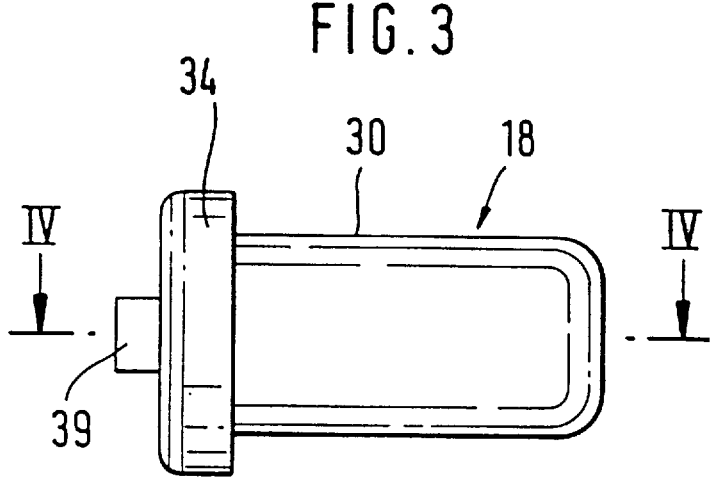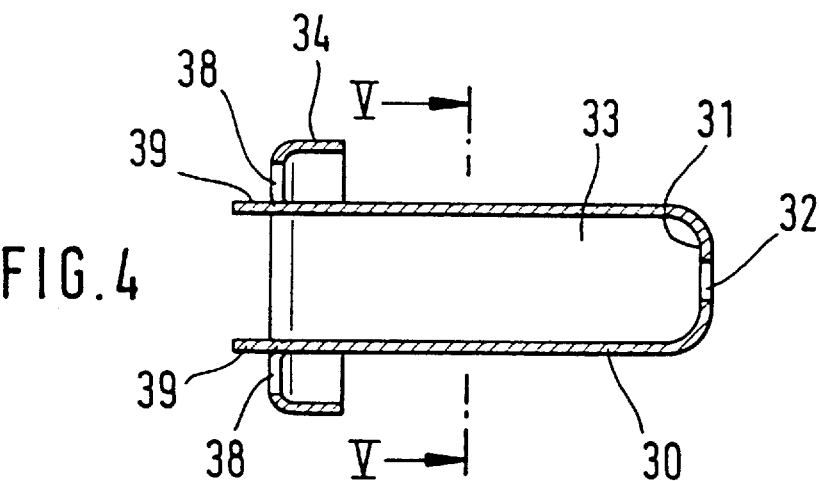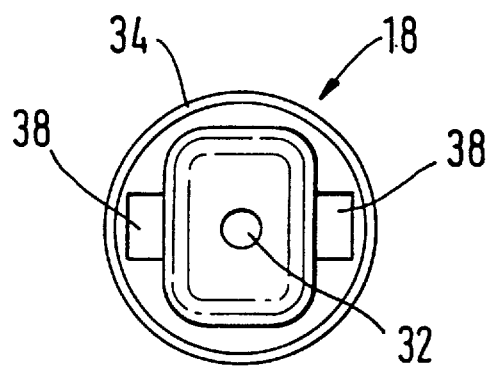

GAS SENSOR

BACKGROUND OF INFORMATION

The present invention proceeds from a gas sensor, in particular for determining the oxygen content in exhaust gases of combustion engines.

U.S. Pat. No. 4,597,850 discloses a gas sensor having a sensor element, in which the sensor element is surrounded at the exhaust-gas end by a double-walled protective tube having an outer cylindrical part and an inner cylindrical part. Gas openings are arranged respectively in the enveloping surface of the outer cylindrical part and at the upper end of the inner cylindrical part, so that between the walls of the cylindrical parts the exhaust gas experiences a deflection. This ensures that the exhaust gas does not flow in a straight line onto the sensitive section of the sensor element. The reason is that if the exhaust gas flowed directly onto the sensor element, the particles entrained in the exhaust gas, for example contaminants or condensed water, might damage the sensitive section of the sensor element.

SUMMARY OF THE INVENTION

The sensor according to the invention has, in contrast, the advantage that the protective tube is of simple construction in terms of manufacturing and assembly. The result of the present invention is that the particles entrained in the exhaust gas of combustion engines, such as for example contaminants or condensed water, are prevented from penetrating into the cavity between the inner and outer protective sleeves. Because of the end-surface opening in the outer protective sleeve, the exhaust gas is additionally deflected at the gas entrance. Another advantage of the present invention is that while the available inside diameter of the outer protective sleeve is small, the sensor element in the inner protective sleeve has sufficient safety clearance on all sides from the inner wall of the inner protective sleeve. This safety clearance is necessary because in the event of an impact load, the sensor element is elastically displaced in the inner protective sleeve, and upon impact against the inner wall would be damaged or could be broken.

It is particularly advantageous to use the gap between the outer protective sleeve and inner protective sleeve as a gas inlet opening and/or gas outlet opening. As a result, no additional production steps are needed in order to manufacture the gas inlet openings and/or gas outlet openings in the outer protective sleeve. The result of arranging the gas inlet openings on the flange of the inner protective sleeve is that the condensed water entrained in the exhaust gas does not directly strike the sensitive region of the sensor element. The configuration of the gas openings, with shield-like wall sections placed on top, enhances this effect. A particularly advantageous embodiment exists when the aforementioned are used in combination.

BRIEF DESCRIPTION OF THE DRAWINGS

FIG. 3 shows a longitudinal side view of the first exemplary embodiment of the gas sensor according to the present invention.

FIG. 4 shows a cross sectional view along the line IV—IV of FIG. 3.

FIG. 5 shows a cross-sectional view along the line V—V of FIG. 4.

FIG. 6 shows a plan view of the first exemplary embodiment of the gas sensor according to the present invention.

DETAILED DESCRIPTION OF THE DRAWINGS

Figure 1:
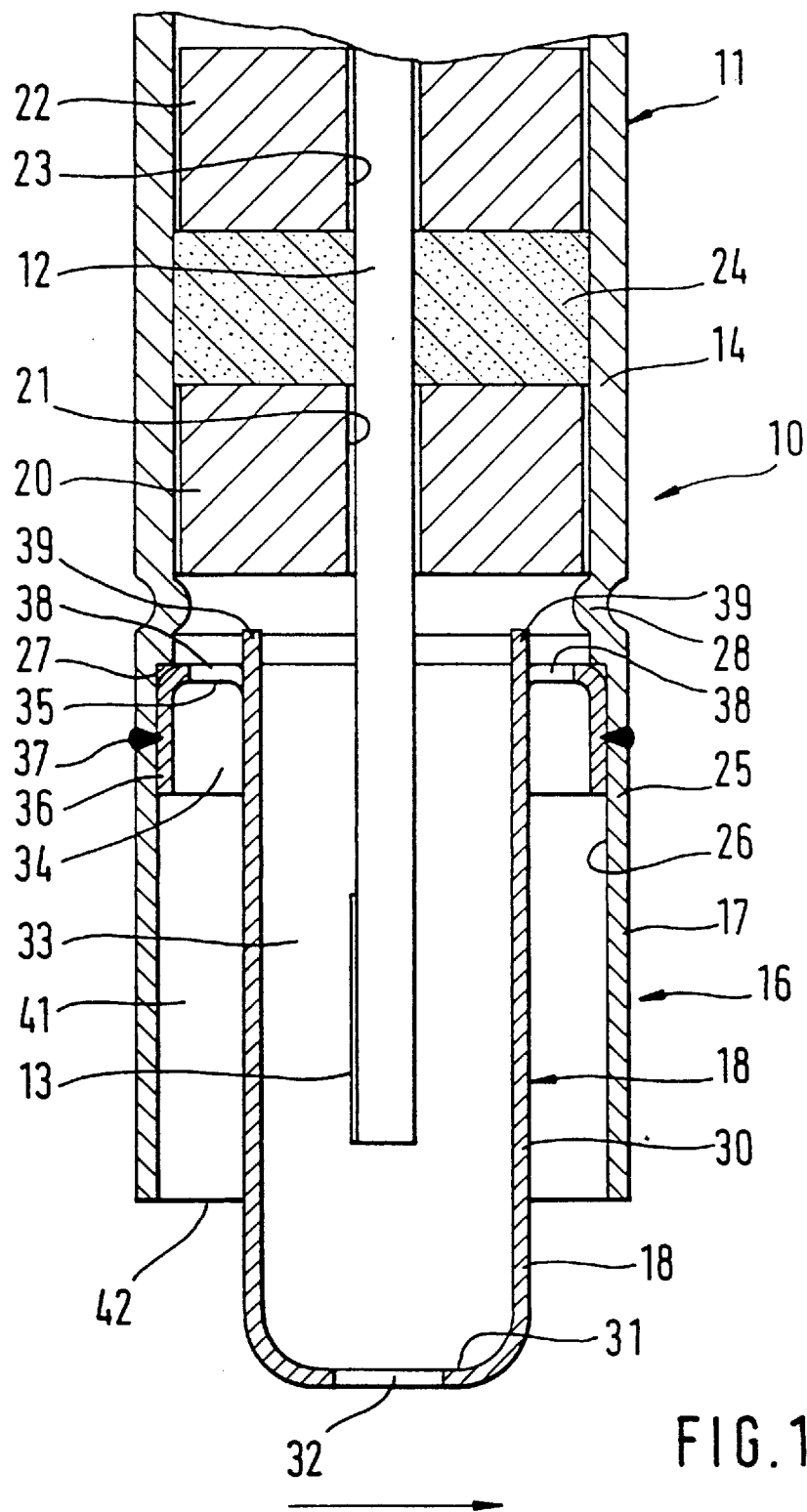
FIG. 1 shows a cross section of a first exemplary embodiment of a gas sensor according to the present invention.

FIG. 1 shows a first exemplifying embodiment of an exhaust gas-end section 10 of a sensor, for example an electrochemical oxygen sensor, having a planar sensor element 12 immobilized in gas-tight fashion in a metal housing 11. Housing 11 is constituted at the exhaust-gas end by a cylindrical housing section 14.

Sensor element 12 consists of an oxygen ion-conducting solid electrolyte ceramic having electrodes (not depicted). At least one electrode is exposed to the exhaust gas, and constitutes a sensitive region 13 on sensor element 12. The planar sensor element 12 is laminated together from multiple ceramic films and sintered, and in the sintered state has a rectangular cross section. Sensitive region 13 of sensor element 12 is surrounded by a double-walled protective tube 16. Protective tube 16 has an outer protective sleeve 17 and an inner protective sleeve 18.

According to the first exemplifying embodiment, outer protective sleeve 17 is constituted by a cylindrical sleeve 25 connected integrally to housing section 14. Cylindrical sleeve 25 extends longitudinally beyond sensor element 12, and has a cylindrical inner wall 26.

A more detailed depiction of inner protective sleeve 18 is evident from FIGS. 3 to 6. Inner protective sleeve 18 has a wall 30 with a base 31 configured at the exhaust-gas end. At the other end, a flange 34 is formed out of wall 30. Wall 30 surrounds a measurement gas space 33 into which sensitive section 13 of sensor element 12 protrudes (FIG. 1). An opening 32 for the entrance and exit of gas is arranged in base 31, aligned with the center line. Flange 34 has a connecting section 35 which extends, for example, at right angles to wall 30, and an attachment section 36 continuous therewith which extends parallel to wall 30 and faces toward base 31. Attachment section 36 is in contact against cylinder wall 26 of sleeve 25 and is attached there, for example, by means of a peripheral laser weld bead or by means of multiple laser spot welds. A peripheral cavity 41, which is open toward the exhaust gas with a radially peripheral gap 42, is present between cylinder wall 26 of sleeve 25 and inner protective sleeve 18 (FIG. 1).

Measurement gas space 33 surrounded by inner protective sleeve 18 has, as shown in FIG. 5, a rectangular cross section corresponding to the rectangular cross section of sensor element 12. Because the cross section of measurement gas space 33 is adapted to the cross section of sensor element 12, the four side surfaces of sensor element 12 are at approximately the same distance from the adjacent wall 30 of inner protective sleeve 18. If measurement gas space 33 had a round cross section, the four edges would extend closer toward wall 30 of inner protective sleeve 18 than the four side surfaces of sensor element 12. Sufficient dimensioning of the round cross section of measurement gas space 33 is not possible, however, if sufficient usable space is not defined by outer protective sleeve 17. In addition, cavity 41 between outer protective sleeve 17 and inner protective sleeve 18 must be sufficiently dimensioned for the exhaust gas to flow through.

Housing section 14 is configured at one point with an indentation 28 projecting radially inwardly. Indentation 28 causes a first ceramic shaped element 20 having a first central passthrough 21, a second ceramic shaped element 22 having a second central passthrough 23, and, arranged between them, a precompressed sealing element 24 made of steatite powder, to be held by a compressive force acting on sealing element 24. The two shaped elements 20, 22 are made, for example, of $Al_2O_3$. The compressive force presses the steatite powder of sealing element 24 against sensor element 12 and against the inner wall of housing section 14, thus holding sensor element 12 in gas-tight fashion in housing section 14. The connection-end part of the sensor, with the contacts for sensor element 12 and the output of the connector cable, will not be discussed further. A variety of embodiments for the connection-end part of gas sensors are sufficiently known.

Exhaust gas flows in the exhaust pipe (not depicted) in the direction indicated by an arrow in FIG. 1; the exhaust gas penetrates via gap 42 into cavity 41 and through openings 38 into measurement gas space 33. Lastly, the exhaust gas flows out of measurement gas space 33 through opening 32. It is not impossible, however, for the exhaust gas also to flow into measurement gas space 33 through opening 32, the flow in measurement gas space 33 and cavity 41 then being reversed.

To facilitate the installation of inner protective sleeve 18, cylindrical inner wall 26 of sleeve 25 has, for example, an annular surface 27 against which protective sleeve 18 makes contact with flange 34. Protective sleeve 18 thus assumes a defined axial position in cylindrical sleeve 25.

Openings 38 are advantageously manufactured by folding, for example, two shield-like wall sections 39 out of the material of wall 30; these extend, for example, parallel to sensor element 12 and thereby prolong wall 30. The configuration of openings 38 with wall sections 39 offers the advantage that the condensed water which may possibly get into cavity 41 as the gas enters is deflected toward shaped element 20. The condensed water evaporates upon striking the heated shaped element 20, and thus cannot cause damage to the ceramic of sensor element 12.

Figure 2:
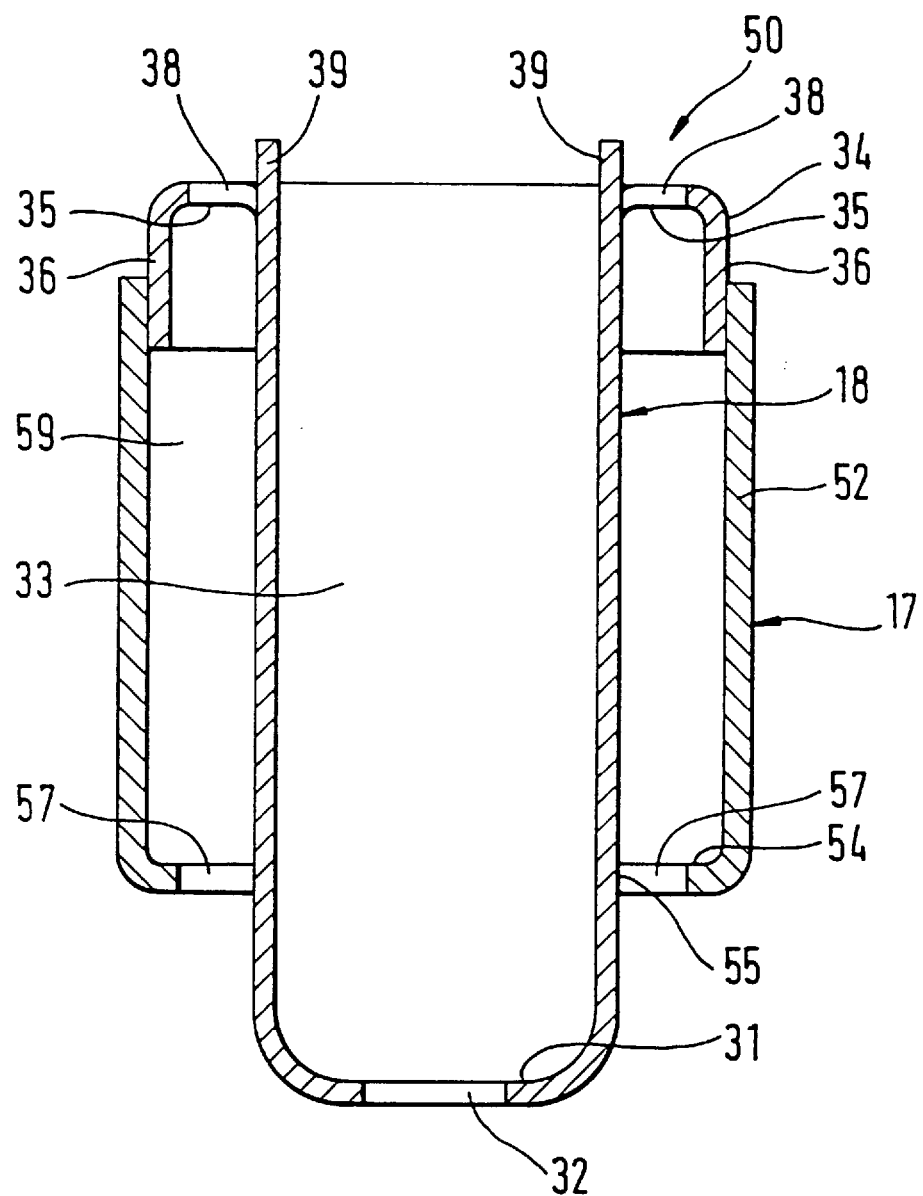
FIG. 2 shows a cross section of a second exemplary embodiment of a gas sensor according to the present invention.

A second exemplifying embodiment is evident from FIG. 2, in which a double-walled protective tube 50 having an outer sleeve 52 (which constitutes outer protective sleeve 17) is provided. Inner protective sleeve 18 of the first exemplifying embodiment is inserted into sleeve 52. Sleeve 52 has a base 54 in which a central opening 55 is present, and through which inner protective sleeve 18 projects. Arranged in base 54 in addition to central opening 55 are further openings 57 which, like gap 42 in the first exemplifying embodiment, allow gas to enter into and/or exit from a cavity 59 configured between sleeve 52 and inner protective sleeve 18. It is also possible, however, to dimension central opening 55 in such a way that a gap for the entry and/or exit of gas is present between inner protective sleeve 18 and the end of sleeve 52.

In contrast to the first exemplifying embodiment, sleeve 52 which constitutes outer protective sleeve 17 is not connected integrally to housing section 14, but is an individual part separate from housing section 14. Otherwise the gas sensor according to the second exemplifying embodiment corresponds to the gas sensor of the first exemplifying embodiment in terms of the housing-end construction. In the case of the gas sensor of the second exemplifying embodiment, however, housing section 14 ends at the location of weld bead 37 of the first exemplifying embodiment.

For better installation of protective tube 50 on housing 11 or housing 14, sleeve 52 is configured with an inside diameter which corresponds to the inside diameter of housing section 14. At the same time, flange 34 of inner protective housing 18 projects out beyond the upper end of sleeve 52. With this projecting section of flange 34, the preassembled protective tube 50 is inserted into the exhaust gas-end opening of housing section 14. Protective tube 50 is then connected to housing section 14 at the contact point at which sleeve 52 and housing section 14 meet, for example by means of a peripheral laser weld bead or by means of laser spot welds. Inner protective sleeve 18, previously immobilized in sleeve 52 solely by means of a press or crimp connection, is also welded during this welding operation.

What is claimed is:

1. A gas sensor, comprising:
a housing;
a sensor element mounted to the housing; and
a double-walled protective tube attached to the housing and surrounding the sensor element, the protective tube including:
an inner protective sleeve having a housing-side opening and an exhaust gas-end opening, and
an outer protective sleeve having a closed enveloping surface and having at least one housing-side opening and an end face with at least one end face opening;
wherein a gas space is formed within the inner protective sleeve and the sensor element projects into the gas space;
wherein a cavity is formed between the outer protective sleeve and the inner protective sleeve;
wherein the at least one housing-side opening of the outer protective sleeve and the housing-side opening of the inner protective sleeve are positioned to allow gas to be conveyed between the gas space and the cavity, wherein the at least one end face opening allows an entry and an exit of gas to and from the cavity, and wherein the exhaust gas-end opening allows the entry and the exit of gas to and from the gas space.

2. The gas sensor of claim 1, wherein the inner protective sleeve includes a flange with a diameter adapted to an inside diameter of the outer protective sleeve and attached to an inner wall of the outer protective sleeve.

3. The gas sensor of claim 2, wherein the flange includes a connecting section and wherein the flange includes the at least one housing-side opening of the outer protective sleeve.

4. The gas sensor of claim 3, wherein the at least one housing-side opening of the outer protective sleeve includes a shield-like wall section shielding the sensor element toward the at least one housing-side opening of the outer protective sleeve.

5. The gas sensor of claim 2, wherein the inner protective sleeve includes a base and the base includes the exhaust gas-end opening, and an additional exhaust gas-end opening.

6. The gas sensor of claim 2, wherein the inner protective sleeve projects beyond the end face of the outer protective sleeve.

7. The gas sensor of claim 1, wherein the at least one end face opening is a radially peripheral gap configured between the outer protective sleeve and the inner protective sleeve.

8. The gas sensor of claim 1, wherein a cross section of the gas space defined by the inner protective sleeve is adapted to a cross section of the sensor element.

9. The gas sensor of claim 8, wherein the cross section of the gas space is rectangular and a distance between an inner wall of the inner protective sleeve and the sensor element is at least approximately uniform in cross section.

10. The gas sensor of claim 1, wherein the outer protective sleeve is formed integrally from the housing.

11. The gas sensor of claim 1, wherein the outer protective sleeve and the inner protective sleeve constitute a preassembled double-walled protective tube arranged on an exhaust-gas end surface of the housing.

12. A gas sensor, comprising:
   a housing;
   a sensor element immobilized in the housing; and
   a double-walled protective tube, including:
      an outer protective sleeve, and
      an inner protective sleeve defining a gas space, wherein the sensor element projects into the gas space;
      wherein a cavity is defined between the outer protective sleeve and the inner protective sleeve;
      wherein the outer protective sleeve has at least one first opening and at least one second opening for an entry and an exit of gas to and from the cavity, wherein the inner protective sleeve has a first opening and a second opening for the exit and the entry of gas to and from the gas space, situated and positioned to allow gas to be conveyed between the gas space and the cavity, and wherein the gas space has a perpendicular cross section adapted to a perpendicular cross section of the sensor element.

13. The gas sensor of claim 12, wherein the perpendicular cross section of the gas space is rectangular.

14. The gas sensor of claim 12, wherein a distance between an inner wall of the inner protective sleeve and the sensor element is approximately uniform in cross section.

* * * * *